(12) United States Patent
Demura et al.

(10) Patent No.: US 11,911,009 B2
(45) Date of Patent: Feb. 27, 2024

(54) LIGHT SOURCE DEVICE, ENDOSCOPE SYSTEM, AND OPERATION METHOD FOR LIGHT SOURCE DEVICE

(71) Applicant: FUJIFILM Corporation, Tokyo (JP)

(72) Inventors: Takanori Demura, Kanagawa (JP); Kenichi Otani, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 17/823,614

(22) Filed: Aug. 31, 2022

(65) Prior Publication Data

US 2023/0073896 A1   Mar. 9, 2023

(30) Foreign Application Priority Data

Sep. 3, 2021   (JP) .................................. 2021-143857

(51) Int. Cl.
*A61B 1/06* (2006.01)

(52) U.S. Cl.
CPC .......... *A61B 1/0655* (2022.02); *A61B 1/0638* (2013.01); *A61B 1/0684* (2013.01)

(58) Field of Classification Search
CPC ... A61B 1/0655; A61B 1/0638; A61B 1/0684; A61B 1/00009
See application file for complete search history.

(56) References Cited

U.S. PATENT DOCUMENTS

| | | | | |
|---|---|---|---|---|
| 4,828,501 A | * | 5/1989 | Ingenito | A61B 1/00135 434/262 |
| 2005/0207157 A1 | * | 9/2005 | Tani | G03B 21/2053 362/613 |

FOREIGN PATENT DOCUMENTS

WO   2018/211600 A1   11/2018

* cited by examiner

*Primary Examiner* — John P Leubecker
*Assistant Examiner* — Jae Woo
(74) *Attorney, Agent, or Firm* — Studebaker & Brackett PC

(57) ABSTRACT

A current having a light emission period current value for emitting first illumination light or second illumination light is caused to flow through a V-LED in a first light emission period for emitting the first illumination light or a second light emission period for emitting the second illumination light. A current having a light non-emission period current value for applying a VF voltage is caused to flow through a pseudo load in a light non-emission period that is provided between the first light emission period and the second light emission period, or between the second light emission periods and in which the first illumination light and the second illumination light are not emitted.

10 Claims, 10 Drawing Sheets

LIGHT SOURCE DEVICE, ENDOSCOPE SYSTEM, AND OPERATION METHOD FOR LIGHT SOURCE DEVICE

CROSS-REFERENCE TO RELATED APPLICATIONS

This application claims priority under 35 U.S.C § 119(a) to Japanese Patent Application No. 2021-143857 filed on 3 Sep. 2021. The above application is hereby expressly incorporated by reference, in its entirety, into the present application.

BACKGROUND OF THE INVENTION

1. Field of the Invention

The present invention relates to a light source device, an endoscope system, and an operation method for the light source device capable of automatically switching and emitting a plurality of pieces of illumination light having different spectra.

2. Description of the Related Art

In the field of endoscopes in recent years, a plurality of pieces of illumination light having different spectra are automatically switched and emitted by using semiconductor light sources of a plurality of colors such as light emitting diodes (LEDs), and image pick-up is performed every emission of each piece of illumination light. For example, in WO2018/211600A, a red LED, a green LED, a blue LED, and the like are used as an illumination unit, and illumination light including a green wavelength band and a plurality of pieces of illumination light including a wavelength band different from green are sequentially switched at a predetermined interval to illuminate a subject.

SUMMARY OF THE INVENTION

In recent years, a CMOS type image pick-up sensor is being used as an image pick-up sensor for picking up an image of an observation target. Since the CMOS type image pick-up sensor performs charge reading for each line, in a case where a plurality of pieces of illumination light are switched as described above, none of the pieces of illumination light are emitted in order to avoid color mixing or image distortion when switching the pieces of illumination light. In this case, when a semiconductor light source is used to emit illumination light, it is necessary to perform switching control for turning the semiconductor light source from a turned-off state to a turned-on state. However, depending on the performance of the switching control, a specific time (rise time for lighting) is required until a necessary amount of light can be emitted from the semiconductor light source switched to a turned-on state. As described above, depending on a length of the rise time for lighting, a tint required for image display may not be obtained.

The present invention provides a light source device, an endoscope system, and an operation method for the light source device capable of instantaneously emitting a necessary amount of light from a semiconductor light source that has been switched to a turned-on state in a case where the semiconductor light source in a turned-off state is switched to a turned-on state.

According to an aspect of the present invention, there is provided a light source device including a plurality of semiconductor light sources, a pseudo load connected to each of the semiconductor light sources, and a light source processor, in which, in a case where the plurality of semiconductor light sources are controlled such that first illumination light and second illumination light having different spectra are automatically switched and emitted according to a specific emission pattern, the light source processor causes a current having a light emission period current value for emitting the first illumination light or the second illumination light to flow through the semiconductor light source in a first light emission period for emitting the first illumination light or a second light emission period for emitting the second illumination light, and causes a current having a light non-emission period current value for applying a VF voltage to flow through the pseudo load in a light non-emission period that is provided between the first light emission period and the second light emission period, or between the second light emission periods and in which the first illumination light and the second illumination light are not emitted.

It is preferable that the light source processor monitors whether or not the VF voltage is applied to the pseudo load, and based on the monitoring result, and controls the current having the light non-emission period current value such that a voltage corresponding to the VF voltage is applied to the pseudo load on the basis of a result of the monitoring. It is preferable that the light source processor determines the VF voltage on the basis of an amount of light emitted from the semiconductor light source in the first light emission period or the second light emission period. It is preferable that the VF voltage is applied to the semiconductor light source at a timing at which the light non-emission period is switched to the first light emission period or a timing at which the light non-emission period is switched to the second light emission period.

The specific emission pattern is preferably any of a first light emission pattern in which the first illumination light is emitted in each first light emission period and the second illumination light having the same spectrum is emitted in each second light emission period, a second light emission pattern in which the first illumination light is emitted in each first light emission period and the second illumination light having a different spectrum is emitted in each second light emission period, or a third light emission pattern in which the first illumination light is emitted in each first light emission period and the second illumination light having a different spectrum is sequentially emitted in the same second light emission period. The plurality of semiconductor light sources preferably include a V-LED, a B-LED, a G-LED, or an R-LED.

According to another aspect of the present invention, there is provided an endoscope system including the above light source device; and an endoscope having a CMOS type image pick-up sensor that sequentially reads accumulated electric charge based on the first illumination light or the second illumination light for each line in the light non-emission period.

According to still another aspect of the present invention, there is provided an operation method for a light source device including a plurality of semiconductor light sources, a pseudo load connected to each of the semiconductor light sources, and a light source processor, the operation method including causing the light source processor, in a case where the plurality of semiconductor light sources are controlled such that first illumination light and second illumination light having different spectra are automatically switched and emitted according to a specific emission pattern, to execute a step of causing a current having a light emission period current value for emitting the first illumination light or the second illumination light to flow to the semiconductor light source in a first light emission period for emitting the first illumination light or a second light emission period for emitting the second illumination light; and a step of causing a current having a light non-emission period current value for applying a VF voltage to flow through the pseudo load in a light non-emission period that is provided between the first light emission period and the second light emission period, or between the second light emission periods and in which the first illumination light and the second illumination light are not emitted.

It is preferable that the light source processor further executes a step of monitoring whether or not the VF voltage is applied to the pseudo load, and a step of controlling the current having the light non-emission period current value such that a voltage corresponding to the VF voltage is applied to the pseudo load on the basis of a result of the monitoring.

According to the present invention, in a case where the semiconductor light source in a turned-off state is switched to a turned-on state, the semiconductor light source switched to the turned-on state can instantaneously emit light having a necessary amount of light.

DESCRIPTION OF THE PREFERRED EMBODIMENTS

Figure 1:
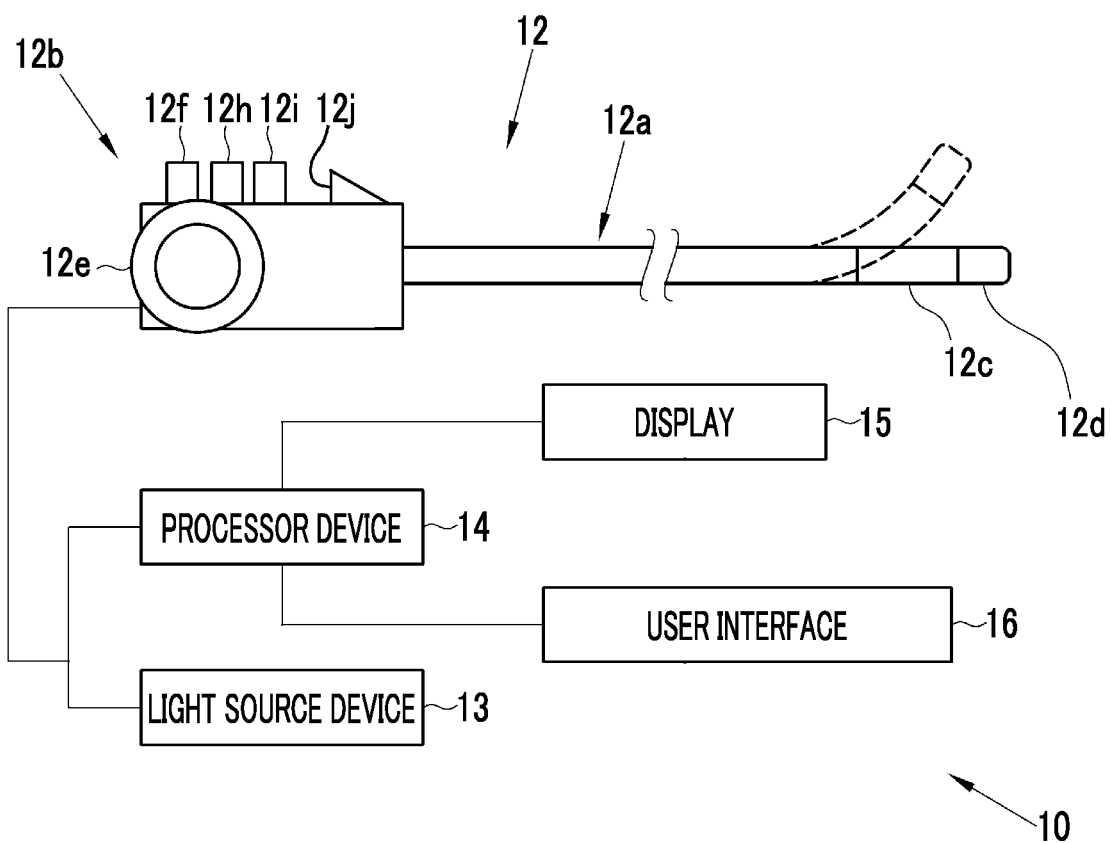
FIG. 1 is a schematic diagram of an endoscope system.

As shown in FIG. 1, an endoscope system 10 includes an endoscope 12, a light source device 13, a processor device 14, a display 15, and a user interface 16. The endoscope 12 is optically or electrically connected to the light source device 13 and electrically connected to the processor device 14.

The endoscope 12 has an insertion part 12a, an operating part 12b, a bendable part 12c, and a tip part 12d. The insertion part 12a is inserted into the body of a subject. The operating part 12b is provided at a base end portion of the insertion part 12a. The bendable part 12c and the tip part 12d are provided on a tip end side of the insertion part 12a. The bendable part 12c is bent by operating an angle knob 12e of the operating part 12b. The tip part 12d is directed in a desired direction in a case where the bendable part 12c is bent. A forceps channel (not shown) for inserting a treatment tool or the like is provided from the insertion part 12a to the tip part 12d. The treatment tool is inserted into the forceps channel from a forceps port 12j.

Inside the endoscope 12, an optical system for forming a subject image and an optical system for irradiating a subject with illumination light are provided. The operating part 12b is provided with an angle knob 12e, a mode selector switch 12f, a still image acquisition instruction switch 12h, and a zoom operating part 12i. The mode selector switch 12f is used for an observation mode switching operation. The still image acquisition instruction switch 12h is used for an instruction for acquiring a still image of a subject. The zoom operating part 12i is used for an operation of enlarging or reducing an observation target.

The light source device 13 generates illumination light. The processor device 14 performs system control on the endoscope system 10 and further performs image processing or the like on an image signal transmitted from the endoscope 12 to generate a medical image or the like. The display 15 displays a medical image transmitted from the processor device 14. The user interface 16 includes a keyboard, a mouse, a microphone, a tablet terminal, a touch pen, and the like, and receives input operations such as function settings.

Figure 2:
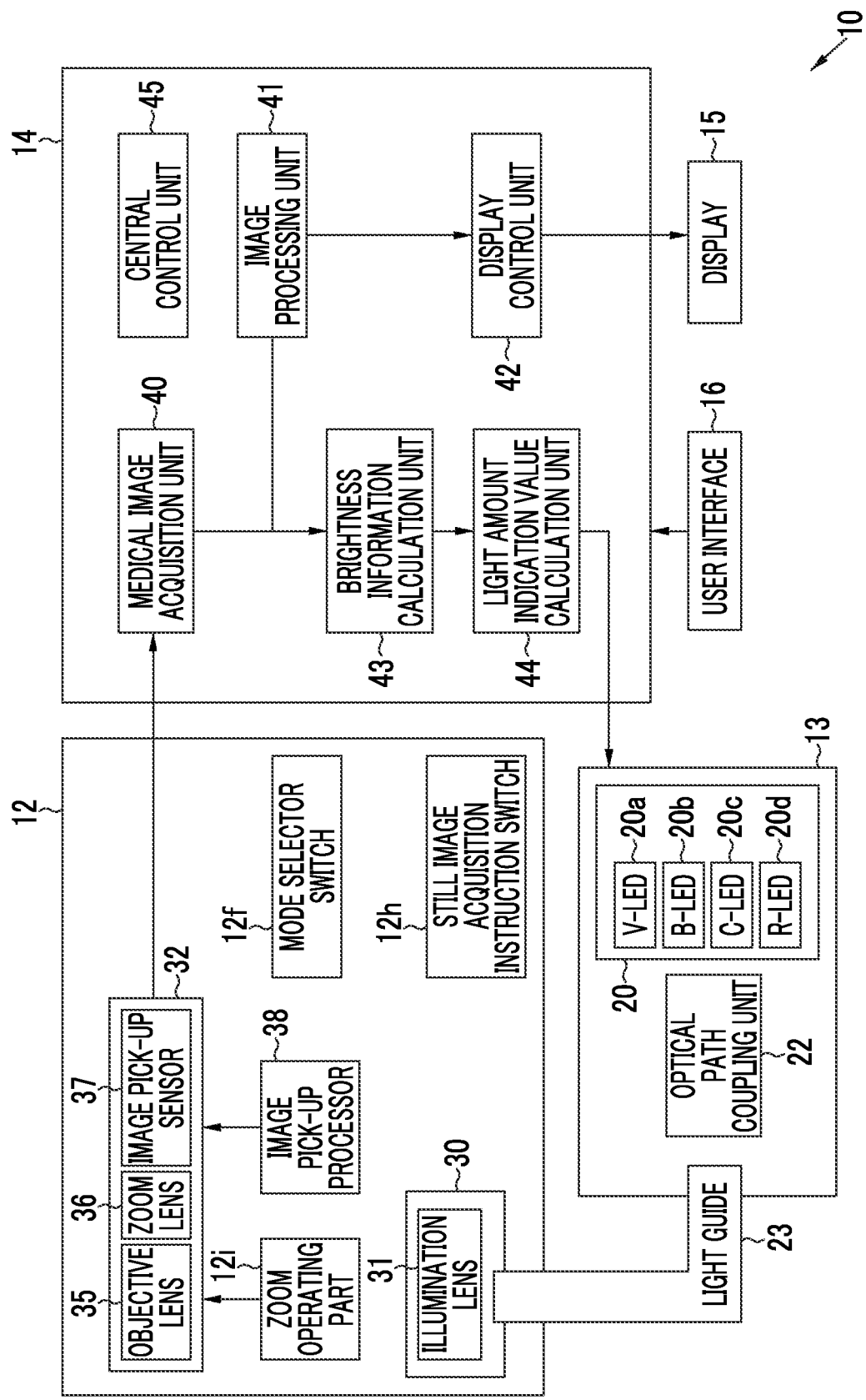
FIG. 2 is a block diagram showing a function of the endoscope system.

In FIG. 2, the light source device 13 includes a light source unit 20 and an optical path coupling unit 22. The light source unit 20 has a plurality of semiconductor light sources, and turns on or off each thereof. In a case where a plurality of semiconductor light sources are turned on, illumination light that illuminates a subject is emitted by controlling an amount of light emitted from each semiconductor light source. The light source unit 20 includes four color LEDs such as a violet light emitting diode (V-LED) 20a, a blue light emitting diode (B-LED) 20b, and a green light emitting diode (G-LED) 20c, and a red light emitting diode (R-LED) 20d. The light source unit 20 may be built in the endoscope 12.

The V-LED 20a generates violet light V having a central wavelength of 405±10 nm and a wavelength range of 380 to 420 nm. The B-LED 20b generates blue light B having a central wavelength of 450±10 nm and a wavelength range of 420 to 500 nm. The G-LED 20c generates green light G having a wavelength range of 480 to 600 nm. The R-LED 20d generates red light R having a central wavelength of 620 to 630 nm and a wavelength range of 600 to 650 nm.

Light emitted by each of the LEDs 20a to 20d is incident to a light guide 23 via the optical path coupling unit 22 configured with a mirror, a lens, and the like. The light guide 23 propagates the light from the optical path coupling unit 22 to the tip part 12d of the endoscope 12.

An illumination optical system 30 and an image pick-up optical system 32 are provided at the tip part 12d of the endoscope 12. The illumination optical system 30 has an illumination lens 31, and the illumination light propagated by the light guide 23 is applied to a subject via the illumination lens 31. On the other hand, in a case where the light source unit 20 is built in the tip part 12d of the endoscope 12, light is emitted toward a subject via the illumination lens of the illumination optical system without using the light guide.

The image pick-up optical system 32 includes an objective lens 35, a zoom lens 36, and an image pick-up sensor 37. Light from a subject due to irradiation with the illumination light is incident to the image pick-up sensor 37 via the objective lens 35 and the zoom lens 36. Consequently, an image of the subject is formed on the image pick-up sensor 37. The zoom lens 36 is a lens for enlarging the subject and is moved between the telephoto end and the wide end by operating the zoom operating part 12i.

The image pick-up sensor 37 is a primary color sensor, and includes three types of pixels such as a blue pixel (B pixel) having a blue color filter, a green pixel (G pixel) having a green color filter, and a red pixel (R pixel) having a red color filter.

The image pick-up sensor 37 is preferably a charge-coupled device (CCD) or a complementary metal oxide semiconductor (CMOS). In the present embodiment, a CMOS type image pick-up sensor is used as the image pick-up sensor 37, but a CCD type image pick-up sensor may be used. The image pick-up processor 38 controls the image pick-up sensor 37. Specifically, an image signal is output from the image pick-up sensor 37 by the image pick-up processor 38 reading a signal of the image pick-up sensor 37. The output image signal is transmitted to the processor device 14.

The processor device 14 has a medical image acquisition unit 40, an image processing unit 41, a display control unit 42, a brightness information calculation unit 43, a light amount instruction value calculation unit 44, and a central control unit 45. In the processor device 14, the central control unit 45 configured with an image control processor operates the program in the program memory (not shown) to realize the functions of the medical image acquisition unit 40, the image processing unit 41, the display control unit 42, the brightness information calculation unit 43, and the light amount instruction value calculation unit 44.

The medical image acquisition unit 40 acquires an image signal from the endoscope 12 as an image signal for a medical image. The image processing unit 41 performs various types of signal processing such as a defect correction process, an offset process, a demosaic process, a matrix process, white balance adjustment, a gamma conversion process, and a YC conversion process on the image signal acquired by the medical image acquisition unit 40. Next, image processing including a 3×3 matrix process, a gradation transformation process, a color conversion process such as three-dimensional look up table (LUT) processing, a color emphasis process, and a structure emphasis process such as spatial frequency emphasis is performed to generate a color medical image. The display control unit 42 displays the medical image generated by the image processing unit 41 on the display 15.

The brightness information calculation unit 43 calculates brightness information indicating the brightness of an observation target from the image signal acquired by the medical image acquisition unit 40. Specifically, the brightness information is calculated by performing arithmetic processing for brightness information such as an average value calculation process or a maximum value calculation process on pixel values of the image signal. The light amount instruction value calculation unit 44 calculates a light amount instruction value for giving a light amount in the light source unit 20 on the basis of a target light amount set in advance and the brightness information calculated by the brightness information calculation unit 43. Specifically, a difference value between the target light amount and the brightness information is calculated, and a light amount instruction value is calculated corresponding to the difference value. The calculated light amount instruction value is transmitted to the light source device 13.

Next, details of light amount control and image pick-up control will be described. The endoscope system 10 includes a mono-light emission mode and a multi-light emission mode as light emission modes for emitting illumination light. By operating the mode selector switch 12f, the light emission modes can be switched via the central control unit 45. The mono-light emission mode is a mode in which illumination light having the same spectrum is continuously applied to illuminate an observation target. The multi-light emission mode is a mode in which a plurality of pieces of illumination light having different spectra are applied while being switched therebetween according to a specific pattern to illuminate a subject.

The illumination light includes first illumination light L1 and second illumination light L2 having a spectrum different from that of the first illumination light. The first illumination light L1 is preferably used for screening observation by giving brightness to the entire subject. The second illumination light L2 is preferably used to emphasize a specific structure such as a duct or a blood vessel of a mucous membrane that is a subject. In the mono-light emission mode, either the first illumination light or the second illumination light is emitted. In the multi-light emission mode, the first illumination light and the second illumination light are switched and emitted according to a specific pattern.

The first illumination light L1 is preferably light having a wide band such as white light. The second illumination light L2 is preferably includes, for example, second illumination light L2SP that emphasizes a superficial blood vessel, second illumination light L2SQ that emphasizes a polar superficial blood vessel shallower than a superficial blood vessel, second illumination light L2SR for generating an oxygen saturation image using a difference in a light absorption coefficient of an oxidized hemoglobin and a reduced hemoglobin, and second illumination light L2SS for generating a color difference expanded image in which a color difference between a plurality of subject ranges is expanded. These four types of second illumination light L2SP, L2SQ, L2SR, and L2SS have different spectra.

In the light source device 13, light amounts of the violet light V, the blue light B, the green light G, and the red light R of four colors are independently controlled, the light amounts are changed, and the first illumination light L1 or the second illumination light L2 (for example, the second Illumination light L2SP, the second illumination light L2SQ, the second illumination light L2SR, and the second illumination light L2SS) are emitted. Light emission control of the mono-light emission mode and the multi emission mode in the light source device 13 is performed by a light source processor (not shown).

In the case of the mono-light emission mode, illumination light having the same spectrum is continuously emitted for each frame. For example, a first illumination light image is displayed on the display 15 by illuminating a subject with the first illumination light for each frame and picking up an image of the subject. A second illumination light image is displayed on the display 15 by illuminating the subject with the second illumination light for each frame and picking up an image of the subject. The frame is a unit of a period including at least a period from the timing of light emission to the completion of reading an image signal in the image pick-up sensor 37.

In the multi-light emission mode, each LEDs 20a to 20d is controlled to automatically switch between the first illumination light and the second illumination light according to a specific emission pattern and to emit light. Specifically, control is performed such that amounts of the violet light V, the blue light B, the green light G, and the red light R are changed for each specific frame F according to a specific light emission pattern.

Figure 3:
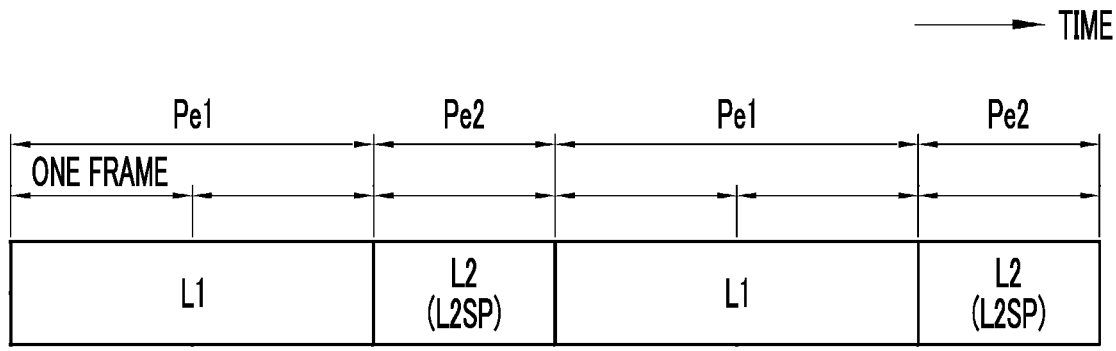
FIG. 3 is an explanatory diagram showing a first light emission pattern.

An example of the light emission pattern is given below. For example, in a first light emission pattern, as shown in FIG. 3, a pattern is repeated in which the first illumination light L1 for two frames is emitted in a first light emission period Pe1 for illuminating the subject with the first illumination light L1, and the second illumination light L2 for one frame is emitted in a second light emission period Pe2 for illuminating the subject with the second illumination light L2. In the first light emission pattern, the same second illumination light L2SP is emitted in each second light emission period Pe2. In the figure, the arrow indicates the direction in which time advances. In the first light emission pattern, the first illumination light L1 having a different spectrum may be emitted in each first light emission period Pe1 (the same applies to the second light emission pattern and a third light emission pattern that will be described below).

Figure 4:
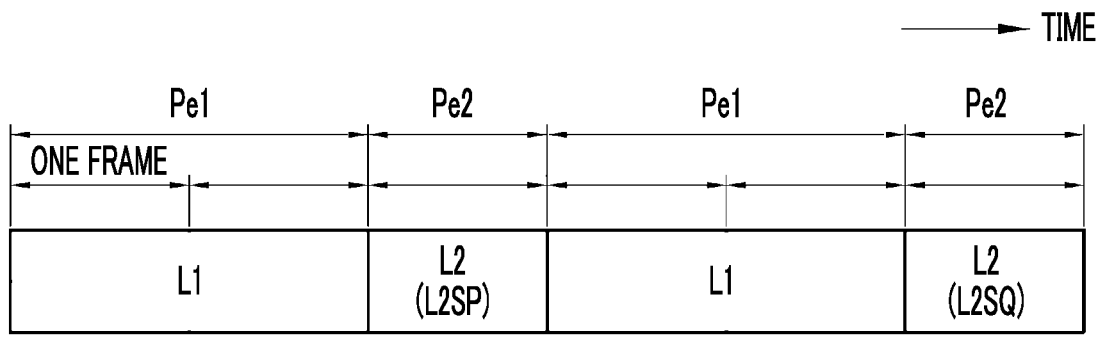
FIG. 4 is an explanatory diagram showing a second light emission pattern.

In a second light emission pattern, as shown in FIG. 4, a pattern is repeated in which the first illumination light L1 for two frames is emitted in the first light emission period Pe1 and the second illumination light L2 for one frame is emitted in the second light emission period Pe2. In this case, in each second light emission period Pe2, the second illumination light L2 having a different spectrum is emitted. Specifically, in the second light emission period Pe2, the second illumination light L2SP and the second illumination light L2SQ are alternately emitted.

Figure 5:
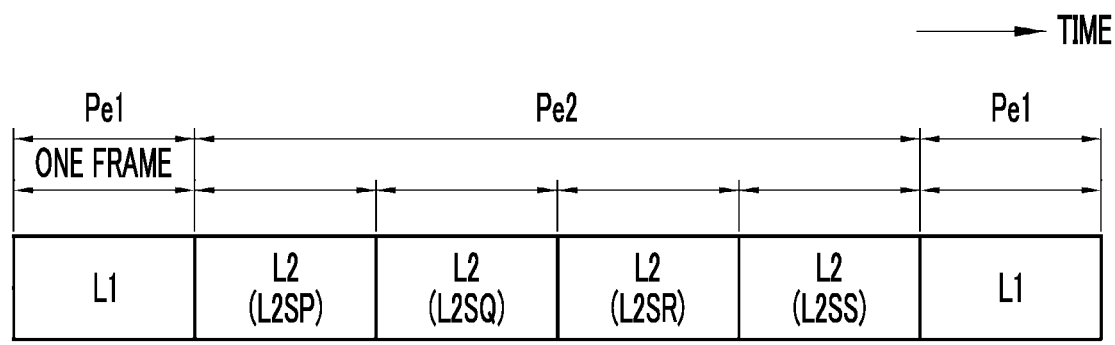
FIG. 5 is an explanatory diagram showing a third light emission pattern.

In the third light emission pattern, as shown in FIG. 5, a pattern is repeated in which the first illumination light L1 for one frame is emitted in the first light emission period Pe1 and the second illumination light L2 for four frames is emitted in the second light emission period Pe2. In this case, in the second light emission period Pe2, as the second illumination light L2, the second illumination light L2SP, the second illumination light L2SQ, the second illumination light L2SR, and the second illumination light L2SS having different spectra are automatically switched and emitted for each frame. In the third light emission pattern, four types of second illumination light L2 having different spectra are switched and emitted, but a plurality of types of second illumination light other than the four types may be switched and emitted.

Figure 6:
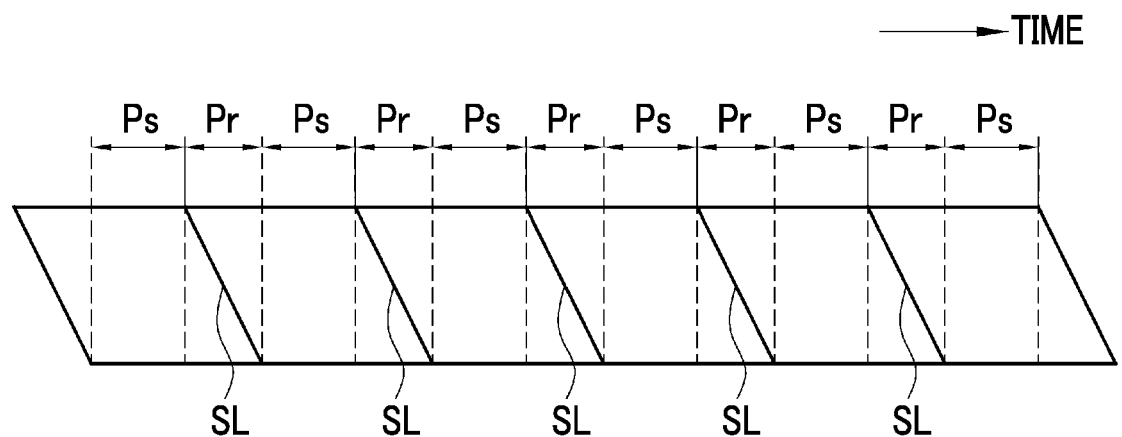
FIG. 6 is an explanatory diagram showing an exposure period and a read period of an image pick-up sensor.

Next, image pick-up control for the image pick-up sensor 37 will be described. As shown in FIG. 6, the image pick-up processor 38 exposes the image pick-up sensor 37 to illumination light from an observation target during an exposure period Ps, and sequentially reads accumulated electric charge for each line of the image pick-up sensor 37 during a read period Pr. In the present embodiment, since a CMOS is used as the image pick-up sensor 37, a diagonal line SL representing the read period Pr represents the time for reading the electric charge from a first line LN1 to a last line LNn. Since the image pick-up sensor 37 has a specific time period as the read period, in the multi-light emission mode, the first illumination light L1 or the second illumination light L2 is not emitted in order to prevent mixing of colors other than a color of illumination light to be read or image distortion in each read period.

Figure 7:
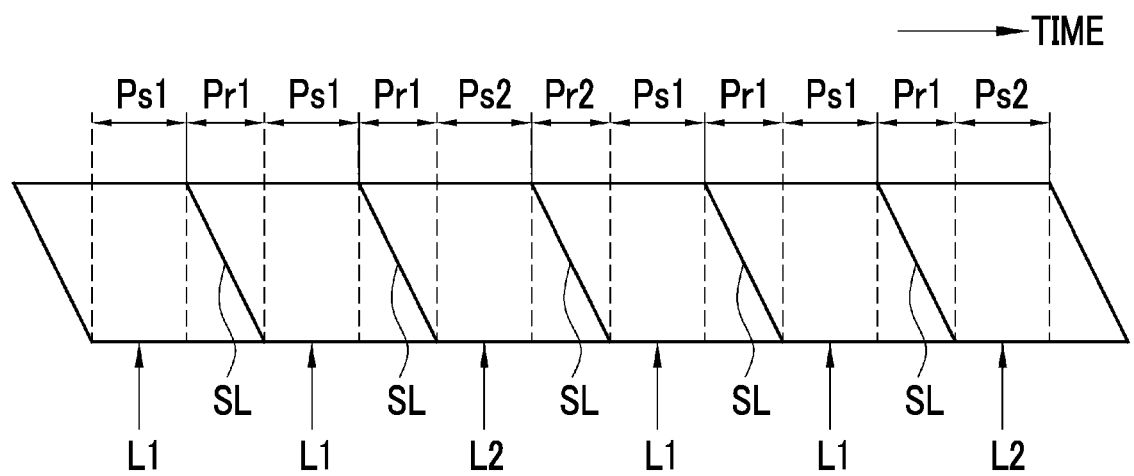
FIG. 7 is an explanatory diagram showing a relationship between the first light emission pattern and the exposure period and the read period of the image pick-up sensor.

As shown in FIG. 7, in the first light emission mode, the image pick-up sensor 37 is exposed to the first illumination light L1 emitted in the first light emission period Pe1 during a first exposure period Ps1 as the exposure period Ps, and after the first exposure period Ps1, electric charge corresponding to the first illumination light L1 is read during a first read period Pr1 as the read period Pr1. During the first read period Pr1, the first illumination light L1 or the second illumination light L2 is not emitted. After the first read period Pr1, the image pick-up sensor 37 is exposed to the second illumination light L2 emitted in the first light emission period Pe1 during a second exposure period Ps2 as the exposure period Ps, and after the second exposure period Ps2, electric charge corresponding to the second illumination light L2 is read during a second read period Pr2 as the read period Pr. During the second read period Pr2, the first illumination light L1 or the second illumination light L2 is not emitted. As for the second light emission mode and the third light emission mode, the same exposure and image pick-up control as in the first light emission mode is performed. The first exposure period and the second light emission period may be the same or different, and the second exposure period and the second light emission period may be the same or different.

Figure 8A:
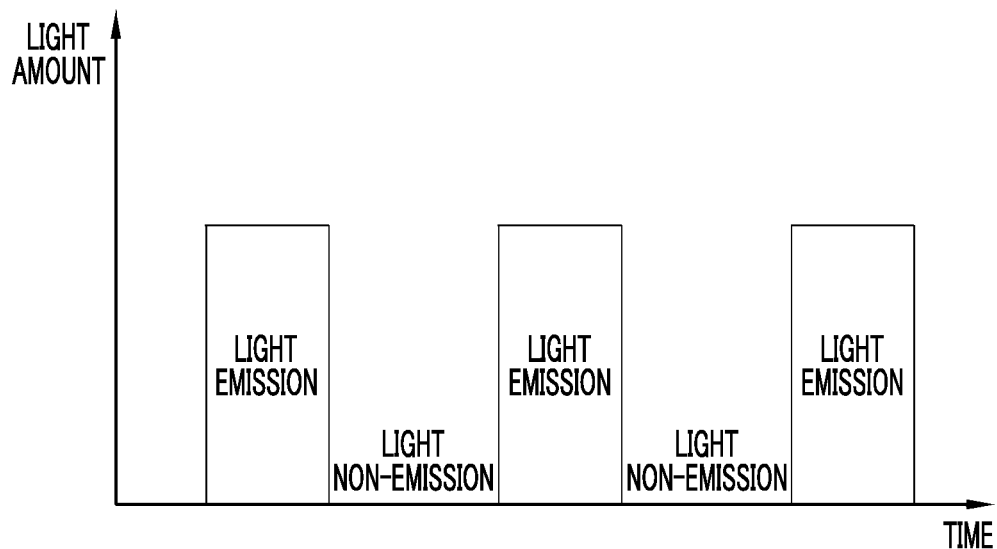
FIG. 8A is an explanatory diagram showing light emission and light non-emission of a V-LED in the present embodiment.
Figure 8B:
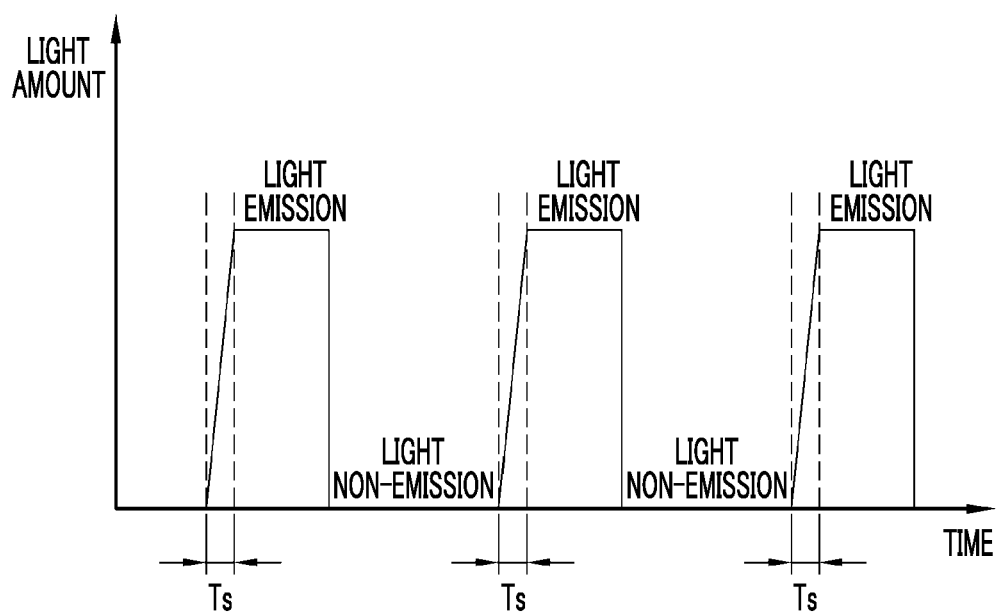
FIG. 8B is an explanatory diagram showing light emission and light non-emission of a V-LED having a specific time as a rise time for lighting.

In the multi-light emission mode, as described above, emission and non-emission of the first illumination light L1 and the second illumination light L2 are repeated. In the present embodiment, in order to eliminate color mixing or image distortion, in the light source unit 20 of the light source device 13, external switching units (a pseudo load switching unit 54 and a light emission control switching unit 55) are provided for the V-LED 20a (refer to below for details). Consequently, as shown in FIG. 8A, emission and non-emission of the first illumination light L1 and the second illumination light L2 are instantaneously switched, and the first illumination light L1 or the second illumination light L2 is emitted only during the exposure period. The rise time for lighting means the time until a light amount of the first illumination light L1 or the second illumination light reaches a necessary intensity LM. FIGS. 8A and 8B show a case of the first light emission mode.

In a case of switching between emission and non-emission of the first illumination light L1 and the second illumination light L2 without using an external switching unit such as the light source unit 20 of the present embodiment, as shown in FIG. 8B, a rise time Ts for lighting of the first illumination light L1 or the second illumination light L2 is required for a specific time, and a light amount that is necessary during the exposure period is insufficient, and thus it is difficult to stabilize a tint of an image. In this case, the rise time for lighting requires a time (several ms) of 10% or more of the exposure period.

Figure 9:
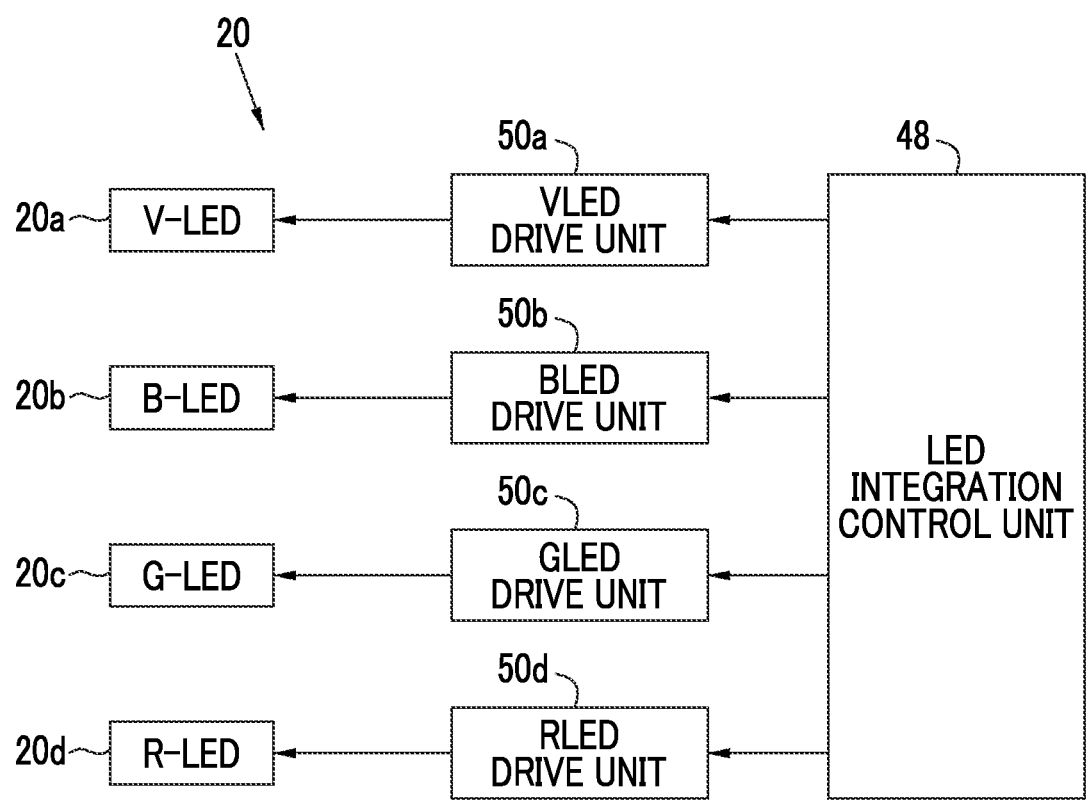
FIG. 9 is a block diagram showing a function of a light source unit.

As shown in FIG. 9, the light source unit 20 includes an LED integration control unit 48, a VLED drive unit 50a controlling the drive of the V-LED 20a, a BLED drive unit 50b controlling the drive of the B-LED 20b, a GLED drive unit 50c controlling the drive of the G-LED 20c, and an RLED drive unit 50d controlling the drive of the R-LED 20d.

In the light source unit 20, programs related to various processes are stored in a program memory (not shown). Functions of the LED integration control unit 48, the VLED drive unit 50a, the BLED drive unit 50b, the GLED drive unit 50c, and the RLED drive unit 50d are realized by the light source processor in the light source unit 20 executing the programs in the program memory. Along with this, as will be described later, functions of a VLED current setting unit 51, a VLED driver 52, a pseudo load 53, a pseudo load switching unit 54, a light emission control switching unit 55, and a VF voltage monitoring unit 58 are also realized.

The LED integration control unit 48 is composed of a field programmable gate array (FPGA), and calculates an amount of light emitted by each of the LEDs 20a to 20d on the basis of a light amount instruction value from the processor device 14. Specifically, a light amount of each LEDs 20a to 20d is set such that a total amount of light emitted by each LEDs 20a to 20d becomes the light amount instruction value. In the multi-light emission mode, the LED integration control unit 48 generates a light emission control signal for causing each of the LEDs 20a to 20d to emit or not to emit light on the basis of each light emission mode (first to third light emission modes) of the multi-light emission mode set by the processor device 14.

Specifically, the LED integration control unit 48 turns on the light emission control signal at a timing at which the light non-emission period is ended and the first or second light emission period is started in the multi-light emission mode, and turns off the light emission control signal at a timing at which the first or second light emission period is ended and the light non-emission period is ended. The first to third light emission modes are set by operating the user interface 16.

Figure 10:
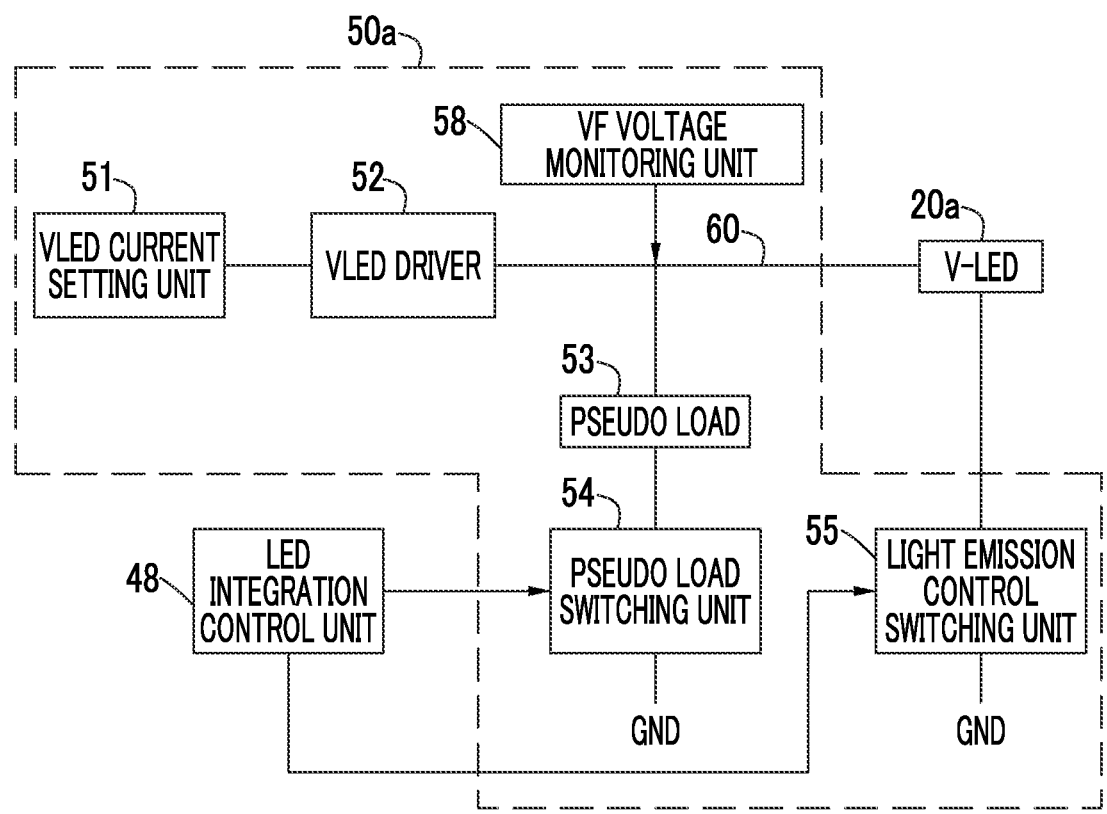
FIG. 10 is a block diagram showing a function of a VLED drive unit.

As shown in FIG. 10, the VLED drive unit 50a includes a VLED current setting unit 51, a VLED driver 52, a pseudo load 53, a pseudo load switching unit 54, a light emission control switching unit 55, and a VF voltage monitoring unit 58. The pseudo load 53 and the pseudo load switching unit 54 are connected to a connection line 60 connecting the VLED driver 52 to the V-LED 20a, and the pseudo load switching unit 54 is grounded by GND. The V-LED 20a is connected to the light emission control switching unit 55, and the light emission control switching unit 55 is grounded by GND. The pseudo load switching unit 54 and the light emission control switching unit 55 are connected to the LED integration control unit 48, and can receive an ON or OFF light emission control signal from the LED integration control unit 48. Since the BLED drive unit 50b, the GLED drive unit 50c, and the RLED drive unit 50d are the same as the VLED drive unit 50a, detailed description and illustration thereof are omitted.

Figure 11:
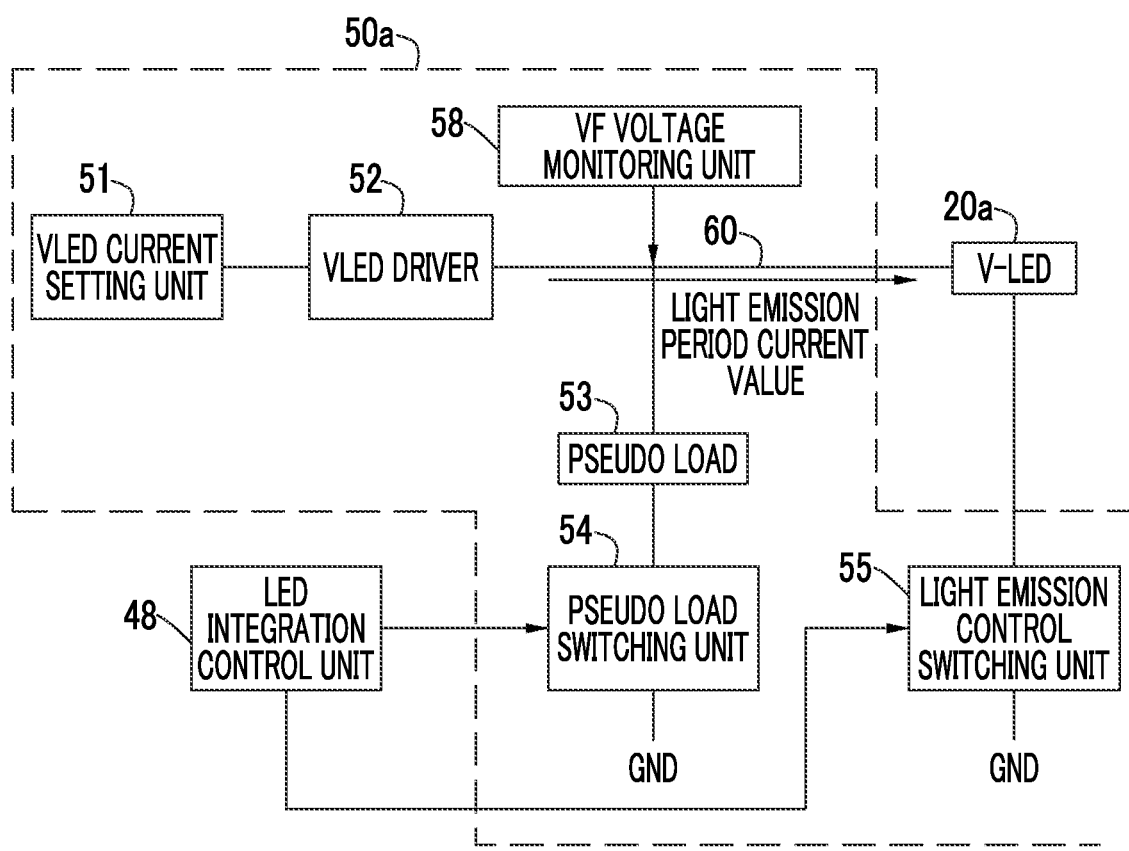
FIG. 11 is an explanatory diagram showing a current flow having a light emission period current value.

The VLED current setting unit 51 sets a light emission period current value required to emit a light amount of the V-LED 20a calculated by the LED integration control unit 48 in the first light emission period or the second light emission period of the multi-light emission mode. As shown in FIG. 11, the VLED driver 52 performs control such that a current having the light emission period current value flows through the V-LED 20a during the light emission period from the time when the light emission control switching unit 55 receives an ON light emission control signal to the time when an OFF light emission control signal is received.

The light emission control switching unit 55 is preferably composed of a field effect transistor (FET). The light non-emission period is preferably provided between the first exposure period and the second exposure period, or between the second light emission periods. It is preferable that the light non-emission period and the first read period match each other, and it is also preferable that the light non-emission period and the second read period match each other. The light emission period current value includes a current value for the first light emission period determined on the basis of an amount of the first illumination light and a current value for the second light emission period determined on the basis of an amount of the second illumination light.

The VLED current setting unit 51 sets a light non-emission period current value required for causing a current corresponding to VF (forward voltage) to flow to the pseudo load 53 in the light non-emission period of the multi-light emission mode. The VF voltage is preferably determined by at least a light amount of the V-LED 20a calculated by the LED integration control unit 48 (an amount of light emitted by the V-LED 20a in the exposure period). It is preferable to determine the VF voltage in consideration of the characteristics of the V-LED 20a.

Figure 12:
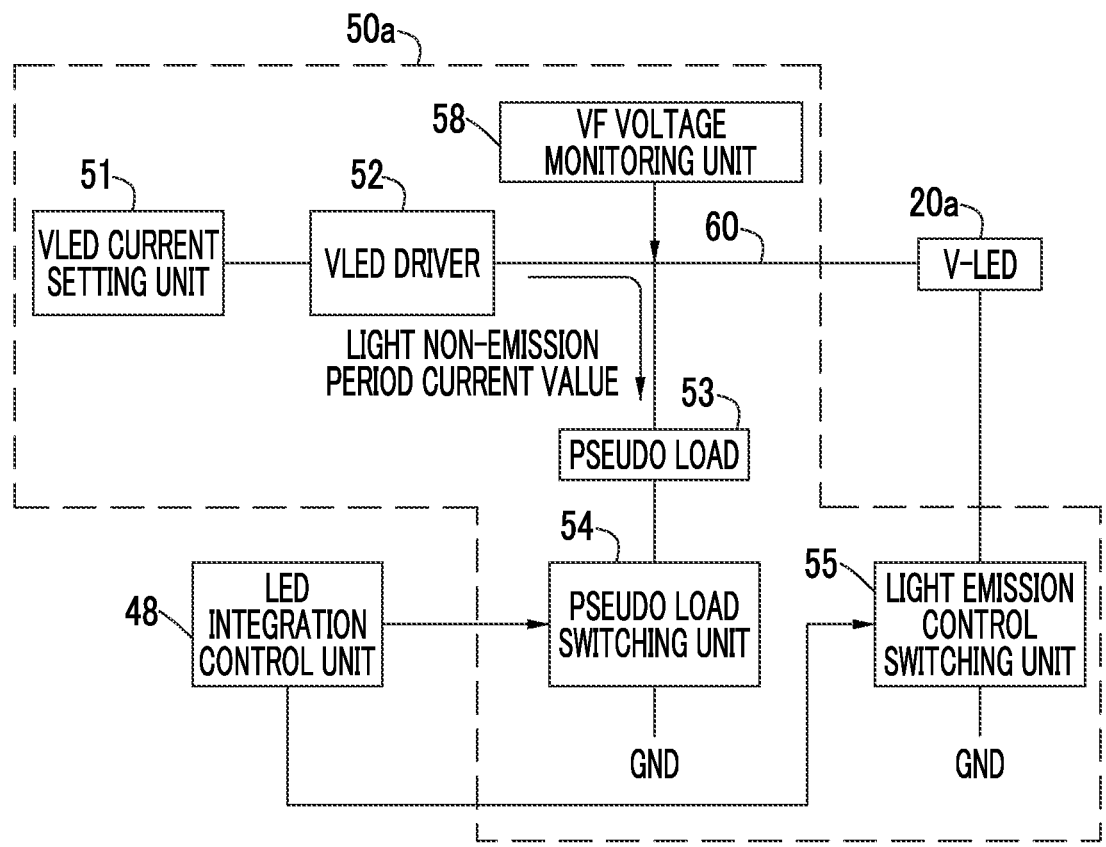
FIG. 12 is an explanatory diagram showing a current flow having a light non-emission period current value.

As shown in FIG. 12, the VLED driver 52 performs control such that a current having the light non-emission period current value flows through the pseudo load 53 during the light non-emission period from the time when the pseudo load switching unit 54 receives an OFF light emission control signal and the time when an ON light emission control signal is received. Consequently, during the light non-emission period, a voltage corresponding to VF is applied to the pseudo load 53 connected to the connection line 60 connected to the V-LED 20a. At a timing at which the light non-emission period is switched to the first light emission period or a timing at which the light non-emission period is switched to the second light emission period, the voltage corresponding to VF is also instantaneously applied to the V-LED 20a. Consequently, the V-LED 20a can be turned on immediately without requiring a rise time. The pseudo load switching unit 54 is also preferably composed of an FET.

The VF voltage monitoring unit 58 is connected to the connection line 60, and monitors whether or not the voltage corresponding to VF is applied to the pseudo load 53 at least during the light non-emission period. A result of the monitoring is transmitted to the VLED driver 52, and the VLED driver 52 controls a current having the light non-emission period current value such that the voltage corresponding to the VF is applied to the pseudo load 53 at least during the light non-emission period. The VF voltage monitoring unit 58 may also perform monitoring during the first light emission period or the second light emission period.

Figure 13:
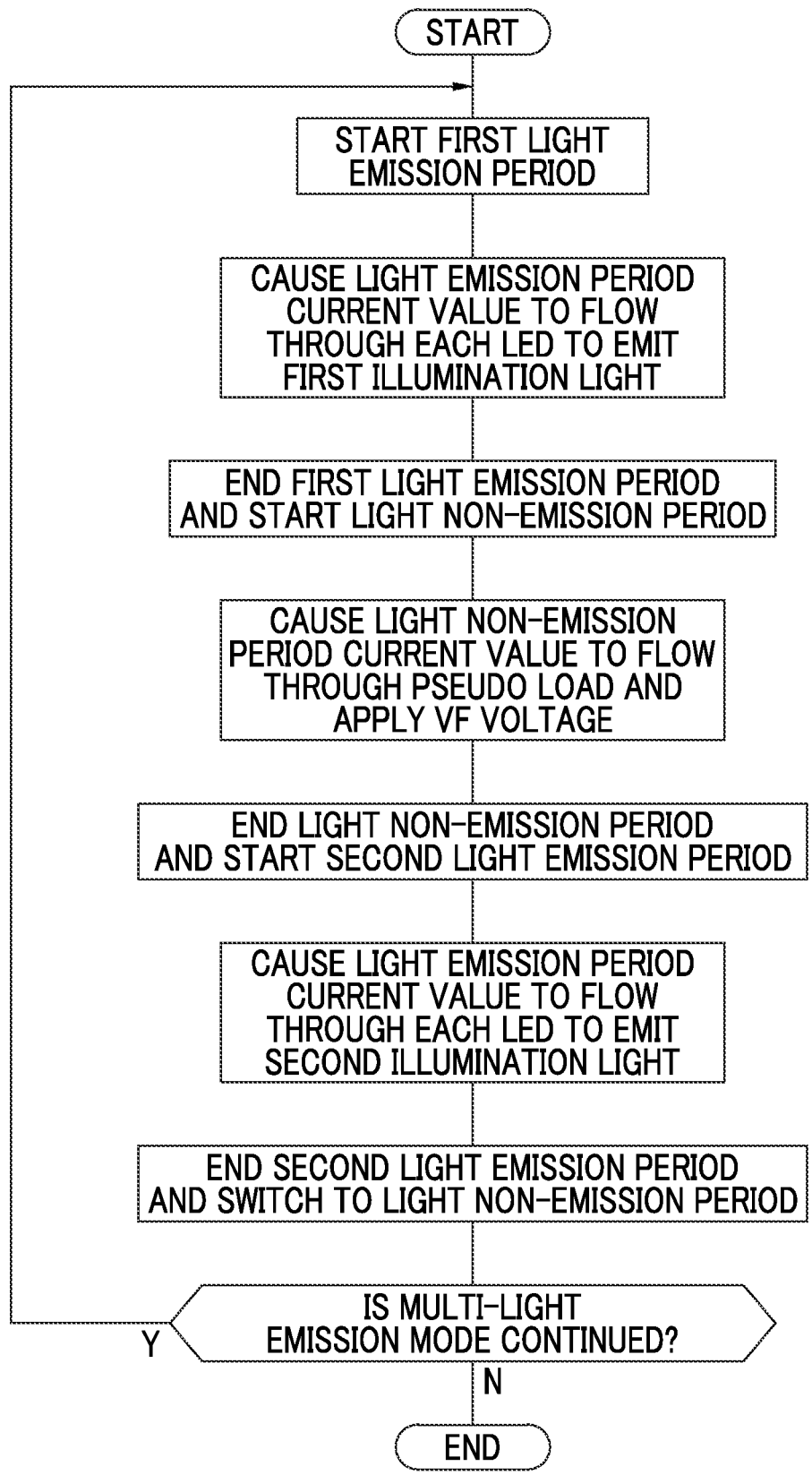
FIG. 13 is a flowchart showing a series of flows in a multi-light emission mode.

Next, a series of flows in light emission control in the multi-light emission mode will be described with reference to a flowchart of FIG. 13. When a mode is switched to the multi-light emission mode, the first light emission period is started, a current having a light emission period current value for emitting the first illumination light flows through each of the LEDs 20a to 20d, and thus the first illumination light is emitted. When the first light emission period is ended, the period is switched to the light non-emission period in which each of the LEDs 20a to 20d is turned off.

During the light non-emission period, a current having a light non-emission period current value for applying the VF voltage to the pseudo load flows through the pseudo load 53. Consequently, a voltage corresponding to VF is applied to a pseudo load (the pseudo load 53 in the case of V-LED 20a) connected to the connection line connected to each of the LEDs 20a to 20d. When the light non-emission period is ended to be switched to the second light emission period, a current having a light emission period current value for emitting the second illumination light flows through each of the LEDs 20a to 20d. At this timing, a voltage corresponding to VF, which is the same as that of the pseudo load connected via the connection line for each LEDs 20a to 20d, is applied to each of the LEDs 20a to 20d. Consequently, immediately after switching to the second light emission period, light having e necessary light amount is emitted from each of the LEDs 20*a* to 20*d*. After the second light emission period is ended, the period is switched to the light non-emission period in the same manner as described above. As long as the multi-light emission mode is continued, the above control is repeatedly performed.

In the above embodiment, hardware structures of processing units executing various processes, such as the medical image acquisition unit 40, the image processing unit 41, the display control unit 42, the brightness information calculation unit 43, the light amount instruction value calculation unit 44, the LED integration control unit 48, the VLED drive unit 50*a*, and the BLED drive unit 50*b*, the GLED drive unit 50*c*, the RLED drive unit 50*d*, the VLED current setting unit 51, the VLED driver 52, and the VF voltage monitoring unit 58 are various processors as described below. The various processors include a programmable logic device (PLD), that is a processor of which a circuit configuration can be changed after manufacturing, such as a central processing unit (CPU), a graphical processing unit (GPU), or a field programmable gate array (FPGA) that is a general-purpose processor that executes software (programs) and functions as various processing units, a dedicated electric circuit that is a processor having a circuit configuration specially designed to execute various processes, and the like.

One processing unit may be configured with one of these various processors, or may be configured with a combination of two or more processors of the same type or different types (for example, a plurality of FPGAs, a combination of a CPU and an FPGA, or a combination of a CPU and a GPU). A plurality of processing units may be configured by one processor. As an example of configuring a plurality of processing units with one processor, first, there is a form in which one processor is configured by a combination of one or more CPUs and software, as typified by a computer used for a client or a server, and this processor functions as a plurality of processing units. Second, as typified by system on chip (SoC), there is a form in which a processor that realizes functions of the entire system including a plurality of processing units with one integrated circuit (IC) chip is used. As described above, the various processing units are configured by using one or more of the above various processors as a hardware structure.

The hardware structure of these various processors is, more specifically, an electric circuit (circuitry) in which circuit elements such as semiconductor elements are combined. A hardware structure of the storage unit is a storage device such as a hard disk drive (HDD) or a solid state drive (SSD).

EXPLANATION OF REFERENCES

10: endoscope system
12: endoscope
12*a*: insertion part
12*b*: operating part
12*c*: bendable part
12*d*: tip part
12*e*: angle knob
12*f*: mode selector switch
12*h*: still image acquisition instruction switch
12*i*: zoom operating part
12*j*: forceps port
13: light source device
14: processor device
15: display
16: user interface
20: light source unit
20*a*: V-LED
20*b*: B-LED
20*c*: G-LED
20*d*: R-LED
22: optical path coupling unit
23: light guide
30 illumination optical system
31: illumination lens
32: image pick-up optical system
35: objective lens
36: zoom lens
37: image pick-up sensor
38: image pick-up processor
40: medical image acquisition unit
41: image processing unit
42: display control unit
43: brightness information calculation unit
44: light amount indication value calculation unit
45: central control unit
48: LED integration control unit
50*a*: VLED drive unit
50*b*: BLED drive unit
50*c*: GLED drive unit
50*d*: RLED drive unit
51: VLED current setting unit
52: VLED driver
53: pseudo load
54: pseudo load switching unit
55: light emission control switching unit
58: VF voltage monitoring unit
60: connection line
L1: first illumination light
L2, L2SP, L2SQ, L2SR, L2SS: second illumination light
Pe1: first light emission period
Pe2: second light emission period
Ps1: first exposure period
Ps2: second exposure period
Pr1: first read period
Pr2: second read period

What is claimed is:

1. A light source device comprising:
a plurality of semiconductor light sources;
a pseudo load connected to each of the semiconductor light sources; and
a light source processor configured to:
control the plurality of semiconductor light sources such that first illumination light and second illumination light having different spectra are automatically switched and emitted according to a specific emission pattern;
cause a current having a light emission period current value for emitting the first illumination light or the second illumination light to flow through the semiconductor light source in a first light emission period for emitting the first illumination light or a second light emission period for emitting the second illumination light; and
cause a current having a light non-emission period current value for applying a VF voltage to flow through the pseudo load in a light non-emission period that is provided between the first light emission period and the second light emission period, or between the second light emission periods and in which the first illumination light and the second illumination light are not emitted.

2. The light source device according to claim 1, wherein the light source processor is further configured to:
monitor whether or not the VF voltage is applied to the pseudo load; and
control the current having the light non-emission period current value such that the VF voltage is applied to the pseudo load on the basis of a result of the monitoring.

3. The light source device according to claim 1, wherein the light source processor is further configured to determine the VF voltage on the basis of an amount of light emitted from the semiconductor light source in the first light emission period or the second light emission period.

4. The light source device according to claim 1, wherein the VF voltage is applied to the semiconductor light source at a timing at which the light non-emission period is switched to the first light emission period or a timing at which the light non-emission period is switched to the second light emission period.

5. The light source device according to claim 1, wherein the specific emission pattern is any of
a first light emission pattern in which the first illumination light is emitted in each first light emission period and the second illumination light having the same spectrum is emitted in each second light emission period,
a second light emission pattern in which the first illumination light is emitted in each first light emission period and the second illumination light having a different spectrum is emitted in each second light emission period, or
a third light emission pattern in which the first illumination light is emitted in each first light emission period and the second illumination light having a different spectrum is sequentially emitted in the same second light emission period.

6. The light source device according to claim 1, wherein the plurality of semiconductor light sources include a V-LED, a B-LED, a G-LED, or an R-LED.

7. An endoscope system comprising:
the light source device according to claim 1; and
an endoscope having a CMOS type image pick-up sensor that sequentially reads accumulated electric charge based on the first illumination light or the second illumination light for each line in the light non-emission period.

8. An operation method for a light source device including a plurality of semiconductor light sources, a pseudo load connected to each of the semiconductor light sources, and a light source processor, the operation method comprising:
causing the light source processor to execute, in a case where the plurality of semiconductor light sources are controlled such that first illumination light and second illumination light having different spectra are automatically switched and emitted according to a specific emission pattern,
a step of causing a current having a light emission period current value for emitting the first illumination light or the second illumination light to flow through the semiconductor light source in a first light emission period for emitting the first illumination light or a second light emission period for emitting the second illumination light; and
a step of causing a current having a light non-emission period current value for applying a VF voltage to the pseudo load in a light non-emission period that is provided between the first light emission period and the second light emission period, or between the second light emission periods and in which the first illumination light and the second illumination light are not emitted.

9. The operation method for a light source device according to claim 8, further comprising:
causing the light source processor to execute
a step of monitoring whether or not the VF voltage is applied to the pseudo load; and
a step of controlling the current having the light non-emission period current value such that the VF voltage is applied to the pseudo load on the basis of a result of the monitoring.

10. The operation method for an endoscope system according to claim 8, wherein
the specific emission pattern is any of
a first light emission pattern in which the first illumination light is emitted in each first light emission period and the second illumination light having the same spectrum is emitted in each second light emission period,
a second light emission pattern in which the first illumination light is emitted in each first light emission period and the second illumination light having a different spectrum is emitted in each second light emission period, or
a third light emission pattern in which the first illumination light is emitted in each first light emission period and the second illumination light having a different spectrum is sequentially emitted in the same second light emission period.

* * * * *